United States Patent
Greco et al.

(10) Patent No.: US 10,217,529 B2
(45) Date of Patent: Feb. 26, 2019

(54) PATIENT BED INVENTORY HARDWARE AND SOFTWARE SYSTEM AND METHOD

(71) Applicant: GetHelp, Inc., Los Angeles, CA (US)

(72) Inventors: Anthony Michael Greco, Los Angeles, CA (US); Andrew Bodis, Los Angeles, CA (US); Thomas A. Sollars, II, Gilbert, AZ (US)

(73) Assignee: GETHELP, INC., Los Angeles, CA (US)

( * ) Notice: Subject to any disclaimer, the term of this patent is extended or adjusted under 35 U.S.C. 154(b) by 0 days.

(21) Appl. No.: 15/869,494

(22) Filed: Jan. 12, 2018

(65) Prior Publication Data

US 2019/0006043 A1     Jan. 3, 2019

Related U.S. Application Data

(60) Provisional application No. 62/526,728, filed on Jun. 29, 2017.

(51) Int. Cl.
*B43L 1/00* (2006.01)
*G16H 10/60* (2018.01)
(Continued)

(52) U.S. Cl.
CPC .............. *G16H 40/20* (2018.01); *B43L 1/004* (2013.01); *G16H 10/60* (2018.01); *G16H 40/40* (2018.01)

(58) Field of Classification Search
CPC ..... G16H 40/20; G06F 19/321; G06F 3/0421; B43L 1/004
See application file for complete search history.

(56) References Cited

U.S. PATENT DOCUMENTS

| | | |
|---|---|---|
| 3,675,204 A | 7/1972 | Miehle |
| 7,555,437 B2 * | 6/2009 | Pierce ............... G06F 19/321 705/2 |

(Continued)

OTHER PUBLICATIONS

Hertzum and Simonsen, Work-Practice Changes Associated with an Electronic Emergency-Department Whiteboard, 2013, Health Informatics Journal, vol. 19, Issue 1, pp. 46-60. (Year: 2013).*

(Continued)

*Primary Examiner* — Christopher L Gilligan
(74) *Attorney, Agent, or Firm* — Cislo & Thomas, LLP

(57) ABSTRACT

A resource tracking system for monitoring the status of multiple resources, displaying the status of those resources to medical personnel, and mirroring the status information to multiple displays for remote users is disclosed. In the preferred embodiment, the tracking system is used to track the availability of beds in a hospital or treatment facility. The resource tracking system comprises a resource tracking board and a server. The board comprises a re-writable surface with a plurality of buttons and lights arrayed in one or more columns; and, a network interface operably coupled to the plurality of buttons and plurality of lights. The lights are configured to emit at least three colors including green when the associated resource is available, yellow when the resource is reserved, and red when the resource is in use. The server is configured to generate interactive displays enabling remote users to observe and reserve available resources. The interactive display features a representation of at least one of the plurality of buttons and lights on the physical board. The server causes any change in status of a resource on the physical board in the hospital or treatment facility to be reflected on the interactive displays. The server also causes any change in status of a resource on an interactive display to be reflected on the physical board in the hospital or treatment facility.

20 Claims, 4 Drawing Sheets

(51) Int. Cl.
*G16H 40/20* (2018.01)
*G16H 40/40* (2018.01)

(56) References Cited

U.S. PATENT DOCUMENTS

| | | | | |
|---|---|---|---|---|
| 2005/0200595 A1* | 9/2005 | Fors | ................... | G06F 3/03546 |
| | | | | 345/156 |
| 2006/0012568 A1* | 1/2006 | Halcrow | ............... | G06F 3/0421 |
| | | | | 345/157 |
| 2009/0261965 A1* | 10/2009 | Cum | ...................... | G06Q 10/02 |
| | | | | 340/521 |
| 2011/0205062 A1 | 8/2011 | Pesot | | |
| 2011/0208541 A1* | 8/2011 | Wilson | ................... | A61G 7/018 |
| | | | | 705/3 |
| 2013/0304542 A1* | 11/2013 | Powell | ............... | G06Q 30/0203 |
| | | | | 705/7.32 |
| 2018/0004384 A1* | 1/2018 | Fitzgerald | ............. | G06F 3/0488 |

OTHER PUBLICATIONS

USPTO, International Search Report and Written Opinion issued in related International Patent Application No. PCT/US2018/13477 dated Mar. 26, 2018, 17 pages.

\* cited by examiner

PATIENT BED INVENTORY HARDWARE AND SOFTWARE SYSTEM AND METHOD

CROSS-REFERENCE TO RELATED APPLICATION

This patent application claims the benefit of U.S. Provisional Patent Application Ser. No. 62/526,728 entitled "A Bed Button and Bed Board patient bed inventory hardware and platform that communicates with a remote database and online inventory system via mobile and web-based applications." filed Jun. 29, 2017, which application is incorporated in its entirety herein by this reference.

TECHNICAL FIELD

This invention relates to the drug and alcohol treatment and recovery facility industry, but its principles and details are also extendable to other fields including, but not limited to, hospitals (both civilian and military), medical facilities, and the hospitality industry.

BACKGROUND

Recent estimates suggest that approximately 23 million Americans are addicted to drugs and/or alcohol. In 2012, the Substance Abuse and Mental Health Services Administration (SAMHSA) estimates that approximately 2.5 million people received care at some type of treatment facility. SAMHSA also recently estimated that the treatment and recovery industry market is approximately $35 billion per year. In other words, it is big business.

Because the treatment and recovery industry is big business, it has been susceptible to significant incidents of fraud and abuse, as reported by, for example, NBC News in June of 2017 regarding aspects of the drug treatment industry in Florida. NBC wrote that, "an investigation by NBC News has found that many of these vulnerable patients have become grist in an insurance fraud mill. Crooked treatment centers partner with "body brokers" and operators of so-called "sober homes" to find patients with good health insurance. Brokers and sober home owners offer those trying to get clean free rent and grocery store gift cards, cigarettes and manicures in exchange for going to a specific treatment center, which pays kickbacks for every client." See, Florida's Billion-Dollar Drug Treatment Industry Is Plagued by Overdoses, Fraud by Riordan Seville, Lisa, Schecter, Anna R., and Rappleye, Hannah (accessed at http://www.nbcnews.com/feature/megyn-kelly/florida-s-billion-dollar-drug-treatment-industry-plagued-overdoses-fraud-n773376).

The incidence of drug and alcohol dependence, including in recent years, a significant spike in opioid dependence, has only increased the prevalence of treatment and recovery facilities. And, because drug and alcohol treatment is often covered by medical insurance, it has, as NPR recently stated, "created new opportunities for insurance fraud." See, Beach Town Tries To Reverse Runaway Growth of 'Sober Homes' by Greg Allen (accessed at http://www.npr.org/sections/health-shots/2017/08/10/537882989/beach-town-tries-to-reverse-runaway-growth-of-sober-homes).

Because alcohol and drug addiction is so serious and potentially life threatening, however, it is not only big business, but it is extremely serious business, which needs to be monitored and controlled to prevent fraud and abuse at the hands of the addict or alcoholic.

In the treatment and recovery facility industry, it is often the case that a counselor or mental health professional will recommend that a particular person enter into treatment. This process, however, can be interfered with, or even hijacked, by sophisticated marketing schemes in which patient brokering occurs. In some cases, "middle men" or patient brokers will present a candidate for treatment to a facility, and the facility will allow the candidate to stay there rent free and provide a "kick back" to the patient broker. The facility benefits because the candidate will be drug tested and allegedly treated (e.g., via group counseling, acupuncture, massage, physical fitness) for a stretch of time, and insurance companies will pay the facility money for providing or administering such services. Such patient brokering is a problem in and of itself. In addition, many of the facilities participating in such schemes are ill-equipped to actually treat their patients, and the instances of drug abuse and drug overdoses by persons admitted to such facilities actually increases, inhibiting recovery efforts.

For the foregoing reasons, there is a need for a system that addresses the foregoing concerns and issues, and minimizes, if not eliminates, the opportunities for fraud, while simultaneously enhancing client service in terms of placing his or her health needs first. This is accomplished through a tailored, real-time system and method of ascertaining inventory of beds or spaces in a treatment facility, recovery facility, sober home, halfway house, psychiatric ward, or the like in a way that eliminates "middle men" and patient brokers that, at present, are involved in the fraudulent schemes and taking of "kick backs" that are unfortunately so prevalent in this field at this time.

SUMMARY

The invention features a tracking system for monitoring the status of multiple resources, displaying the status of those resources to workers that can act on that information, and mirroring the status information to multiple displays where remote users can make informed decisions about healthcare treatment options based on the availability of those resources. In the preferred embodiment, the tracking system is used to track the availability of beds in a hospital or treatment facility, for example. The availability of beds is displayed to medical staff in the hospital as well as to off-site medical professionals that need to see and know in real-time the availability of, or actually reserve, beds for patients, for example.

In the preferred embodiment, the resource tracking system comprises a resource tracking board and a server. The board comprises a wall-mounted or easel-mounted re-writable surface with a plurality of buttons and lights arrayed in one or more columns (or rows); and a network interface operably coupled to the plurality of buttons and plurality of lights. The lights are configured to emit at least three colors including green when the associated resource is available, yellow when the resource is reserved, and red when the resource is in use or otherwise unavailable.

The system also includes a server configured to generate webpages or other type of interactive displays enabling remote users to observe resources that are available and reserve those resources, if desired. The interactive display features a representation of at least one of the plurality of buttons and lights on the physical board. The server causes any change in status of a resource on the physical board in the hospital to be reflected on the interactive displays. Similarly, the server causes any change in status of a resource on an interactive display to be reflected on the physical board in the hospital.

In some embodiments, the server includes a database of information about a plurality of resources associated with the plurality of lights, including the types of medical services available to patients. This information may be searched by remote medical professionals, law enforcement, social workers, and the public when determining the suitability of a particular facility for a patient. The system may be searchable to determine an optimal facility for a patient, including by location, services provided, types of insurance accepted, and price to name a few exemplary criteria. If desired, the medical professional may reserve a bed for their patient in real-time concurrent with the search.

In some other embodiments, the database includes a comprehensive record of patient information and the board includes a LCD (liquid crystal display) display for displaying a portion of this patient information. In this embodiment, the resource tracking system includes a Health Insurance Portability and Accountability Act (HIPAA) filter configured to prevent the display of any unauthorized patient information to the public.

In addition, the principles of the invention described herein are applicable in other contexts such as hospitals (both civilian and military), medical facilities, nursing homes, shelters, retirement homes, prisons and jails, and the hospitality industry. For example, medical professionals or emergency medical technicians can use the system described herein (in conjunction with a civilian hospital) to ascertain availability of beds or spaces in a hospital or its emergency room to determine the optimal location to deliver a patient.

In a military context, a battlefield may have several mobile "hospital" facilities set up in the vicinity of the battle, and the system described herein can be used to ascertain which facility is best able in terms of availability, capability, and geographical desirability to receive an injured soldier.

In the hospitality industry, the present system can be utilized to ascertain available inventory of rooms in hotels based on specific criteria, as well as by hotels to better manage their inventory of available rooms.

Thus, the present invention can be applied and used in a variety of contexts.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1:
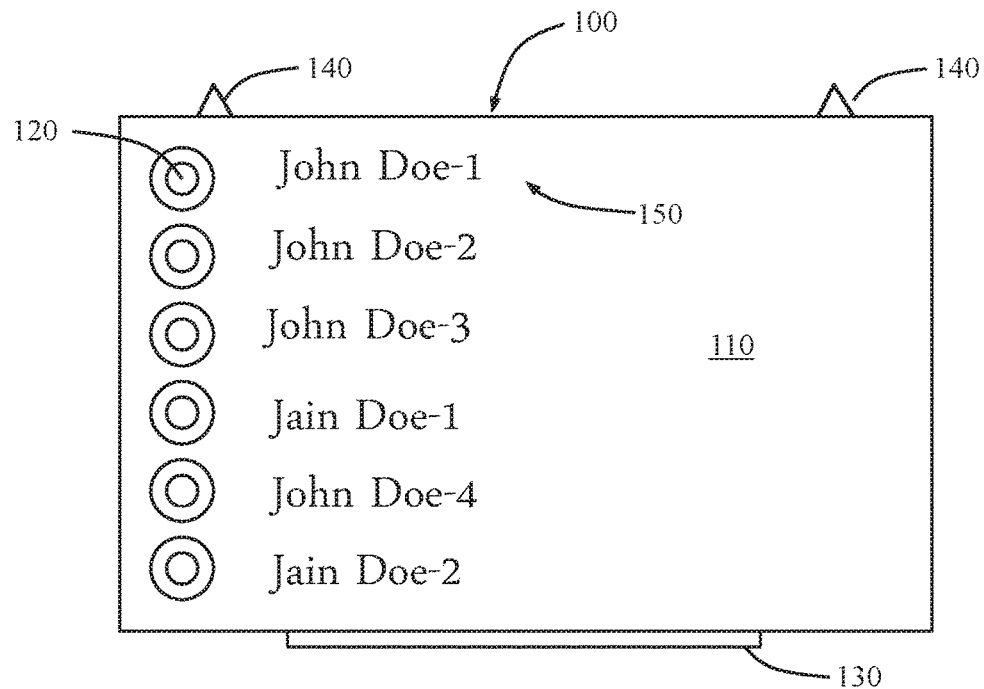
FIG. 1 is a front view of a bed board, in accordance with one embodiment of the present invention.

Illustrated in FIG. 1 is a front view of a bed board 100, which consists of a board 110 having a re-writable surface and a plurality of light buttons 120. The board in the preferred embodiment is an erasable marker board also known as a whiteboard. The whiteboard 110 is configured to be written on with erasable ink from a dry-erase marker, for example. The erasable ink is clearly legible on the board until the ink dries and is erased from the whiteboard 110. The board generally returns to a plain white appearance when the markings have been erased, thus enabling the whiteboard to be repeatedly written on and erased. The process of marking and erasing the whiteboard may be repeated countless times with little or no degradation of the writing surface.

In the preferred embodiment the whiteboard is a homogenous surface having a white finish that is approximately three to six feet wide and approximately two to five feet tall. As one skilled in the art will appreciate, the height and width may vary significantly depending on the application, and are not intended to limit the invention in any way. The bed board may include a horizontal tray 130 affixed to an edge of the whiteboard to hold dry-erase markers and erasers.

The bed board 100 further includes a plurality of light buttons 120 affixed to the front face of the whiteboard. In the preferred embodiment, the light buttons 120 are arrayed in one or more vertical columns with a vertical spacing between each light button of approximately up to two to six inches. Each light button is associated with one resource in a facility in which the bed board is deployed. In some embodiments, the whiteboard 110 includes a plurality of modular whiteboard tiles configured to connect and disconnect to one another. Each whiteboard tile may include one or more light buttons, thereby enabling a facility to increase or decrease the overall size of the whiteboard 110 and tracking capability when the number of beds is increased or decreased, respectively. In some other embodiments, the whiteboard 110 includes an LCD display with a touch-screen interface that enables people to "write" words on the whiteboard with their finger or stylus instead of an erasable marker.

In the preferred embodiment, the facility may be a hospital or treatment facility, and each light button is associated with a bed where a patient may be treated, recuperate, recover, or convalesce. The bed board may be configured to be mounted to a wall in the hospital. As such, the bed board further includes fasteners 140 to hang or otherwise mount the bed board to the wall. The fasteners 140 may include straps, hooks, loops, screws, nails, or a combination thereof. In other embodiments, the bed board may also be mounted to an easel, including an easel with wheels.

In some embodiments, the bed board 100 may further include permanent lines or other indicia (not shown) to define a grid comprising one or more rows (or columns) in which patient information may be written with dry-erase markers, for example. Each row includes one light button and as well as space for writing in the name 150 and other data of the patient occupying the bed associated with the corresponding light button.

In the preferred embodiment, the each light button 120 is configured to emit one of three colors at any given time, namely green, yellow, or red. Each of the buttons is also configured to emit one color and then change color when the light button is pushed. The pushing of the button activates circuitry configured to change the color emitted by the light button. The color change follows a sequence from green, to yellow, to red. For example, the light button is configured to turn yellow if pushed when emitting green light, turn red if pushed when emitting yellow light, and turn green if pushed when emitting red light. In this manner, a nurse or other appropriate facility employee can conveniently and easily change the color of the light.

The color of the light button then signals the availability of the bed associated with the light button. In the preferred embodiment, the light button is set to green to indicate that the associated bed is available to be used or to be reserved for a patient. If and when the associated bed undergoing reservation, the light button is depressed to turn the color to yellow to indicate that the bed is officially, or formally, reserved for a patient. When the patient arrives and is taken to the bed, the light button is depressed again to turn the color red thus indicating to the entire facility (and beyond) that the bed is occupied. Upon arrival, the patient's name and other relevant information may be written on the board next to the associated light button using a dry-erase marker. The light button remains red until the patient is discharged from or otherwise leaves the facility, at which point the light button is depressed again to change its color to green again. The patient name and information may also be erased concurrently while readying the room for the next patient, thus enabling the associated bed to be reserved and occupied once again.

Figure 2:
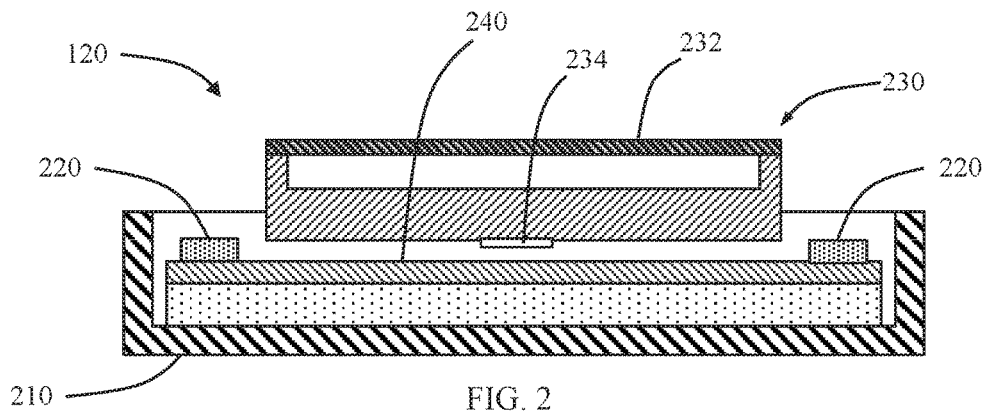
FIG. 2 is a cross section of a light button, in accordance with one embodiment of the present invention.

FIG. 2 is a diagrammatic cross section of a light button, in accordance with one embodiment of the present invention. The light button includes a housing 210, a plurality of LED lights 220, a switch 230, and electronics configured to set the light color and communicate with a server via the Internet, for example. The housing is generally mounted onto the whiteboard 110 or through the whiteboard, depending on the device. The plurality of LED lights 220 include at least one green LED light, at least one yellow LED light, and at least one red LED light, either separate or integrated together. The color of the light emitted is changed by manually depressing the switch plate 232, which causes the electrical contact 234 to engage a circuit board 240 and activate a circuit that turns off one color of LED light and turns on the next color of LED light.

The light button may include a fourth LED light (not shown) whose color indicates the "type" or "class" of resource associated with the light button. The fourth LED light is independent of the green/yellow/red light system and used, for example, to indicate that the associated bed may be utilized for detoxification treatment of patients. In some embodiments, the light button includes a small speaker configured to make a tone or other audible sound when the color of the associated LED light changes.

In other embodiments, the LED lights 220 are configured to generate light patterns, text, graphics, and/or audio tones to communicate various data to the nurses on the hospital floor, or location in the treatment facility. Blinking lights, lights with a circular distribution of LEDs that lite up in a circular pattern, or text, for example, may be encoded in the button light to communicate information relevant to the patient's care, for example.

In the preferred embodiment, the light buttons 120 are "Photon Internet Buttons" manufactured by Particle Industries, Inc. located in San Francisco, Calif. These are wired or wireless devices that include a USB port for communicating Ethernet or Transmission Control Protocol/Internet Protocol (TCP/IP) messages with a wireless router in the facility, for example. The messages, which are explained in more detail below, enable each button to share its status with a remote server, or receive commands to change its status from the server.

Figure 3:
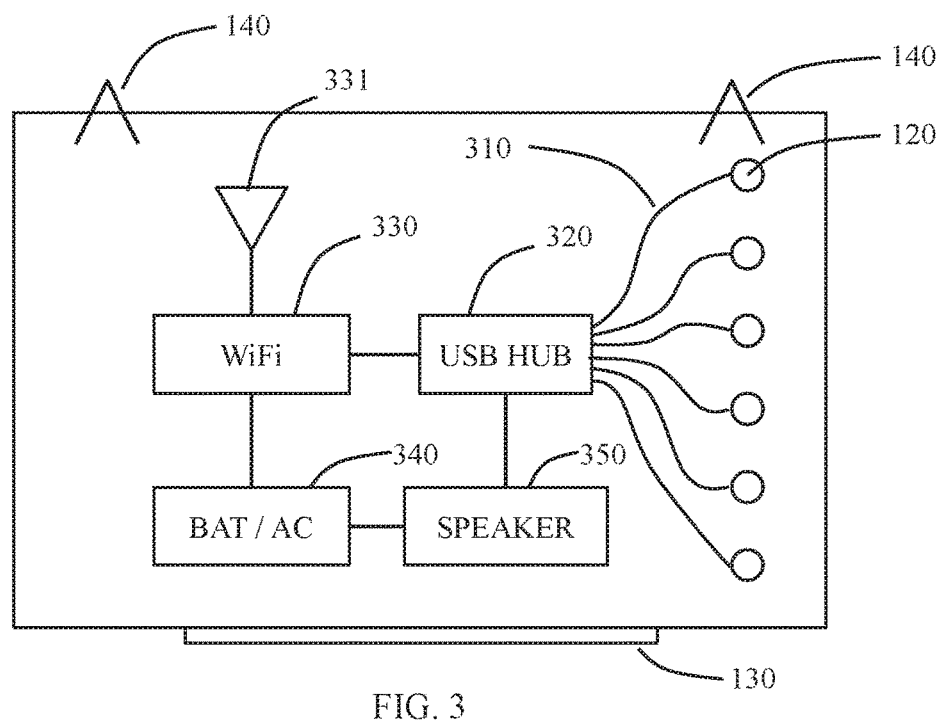
FIG. 3 is a backside view of the bed board, in accordance with one embodiment of the present invention.

Illustrated in FIG. 3 is a backside view of the bed board 100, in accordance with one embodiment of the present invention. As shown, the bed board includes various components mounted to the back of the whiteboard or internally to the whiteboard. These components include USB cables 310 that couple the backs of the light buttons 120 to a network hub or router 320, which is operably coupled to WiFi antenna 330-331 for communicating data messages between the light buttons and the remote server with button color control logic. The WiFi antenna 330-331 may be powered by a battery 340, an AC power outlet, a battery backup, or a combination thereof. The bed board 100 may further include a speaker configured to sound an alarm when a medical "code red", "code blue", or facility-wide emergency is declared. In the case of modular whiteboard tiles, the hub or router 320, WiFi antenna 330-331, and a battery 340 may reside on a single tile referred to herein as a "master" whiteboard tile. Other tiles, called "slave" whiteboard tiles, consisting of one or more light buttons may connect to a single master whiteboard tile and utilize the hub, router, WiFi antenna, and battery of the master whiteboard tile to increase modularity and reduce expense.

Figure 4:
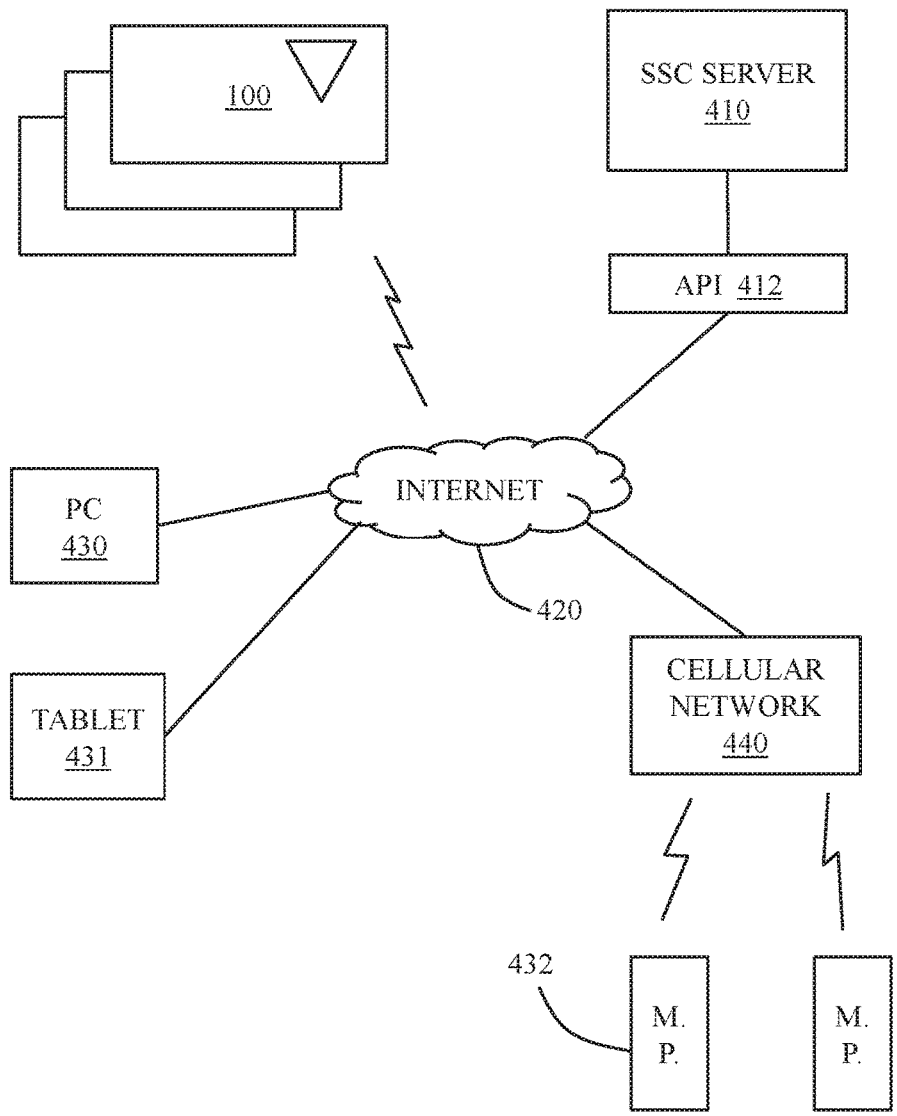
FIG. 4 is a network diagram including a bed board, in accordance with one embodiment of the present invention.

In the preferred embodiment, the bed board 100 is an Internet-enabled device configured to interact with a plurality of other devices for viewing bed status, reserving beds, and otherwise interacting with the bed board. A network diagram of this communication network is shown in FIG. 4, which illustrates a plurality of bed boards 100 that communicate with a server 410 via an application programming interface 412 to the Internet 420, for example. The server 410 includes computer readable code configured to interact with the light buttons of each of the plurality of bed boards 100 in the hospital or facility. In the preferred embodiment, each of the light buttons 120 is configured to send, and the server 410 configured to receive, a message indicating that the button was depressed. In some embodiments, the server is configured to execute an authorization procedure that seeks approval from hospital staff before the light button may change color. In this scenario, the server 410 is configured to transmit a command to the identified light button to change the color of the light emitted only after the proper authorization is received. The actual change in color will depend on the color emitted immediately before the button was depressed. The availability status of a bed or other resource may also be wireless transmitted to and displayed by multi-color light fixtures mounted at the hospital rooms or at the individual patient beds to notify people of the availability of a bed at the bed itself.

In the preferred embodiment, the status of the beds associated with the plurality of light buttons are visible by remote computing devices including personal computers 430, wireless devices 431, and mobile phones 432 using cellular data communication networks 440, for example. A digital representation of the light buttons of the bed board is generated by the server 410 and made available to the remote computing devices 430-432 via interactive webpages or mobile applications. In particular, the server 410 is configured to synchronize the digital representations of the bed boards with the physical bed boards 100 in real-time. When the status of a light button 120 is changed by pressing the button, for example, the change causes the digital representation of the bed boards viewed on the remote computing devices 430-432 to be updated. The remote computing devices and mobile devices may therefore be used by hospital/facility administrators, off-site health practitioners, and law enforcement, for example, to check the availability of a bed the moment it is needed and reserve that bed without the need to be physically present at the hospital/facility to determine if beds are available.

Figure 5:
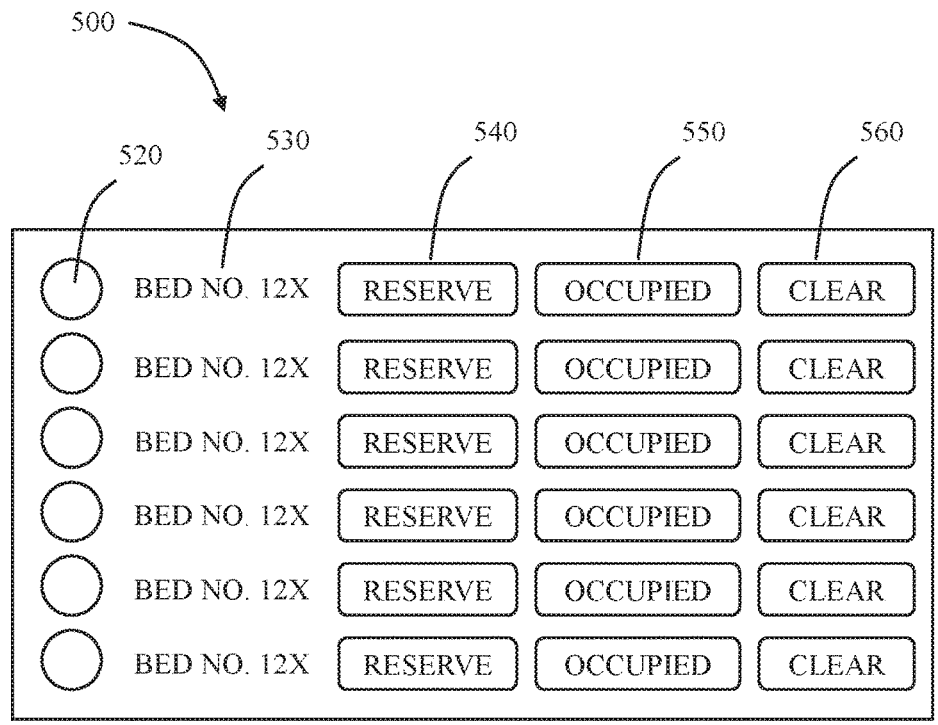
FIG. 5 is a webpage representation of a bed board is seen on a remote computing device, in accordance with one embodiment of the present invention.

In addition to viewing the status of the bed board light buttons, the digital representation of the bed boards may also be used to reserve beds, request reservations for beds, or otherwise change the status of a light button. As shown in FIG. 5, the digital representation 500 of a bed board includes a facsimile 520 of one or more light buttons 120. The facsimile 520 of each light button may be configured in HTML (or HTML5, for example) to change the color of the light button when the user clicks on it using a mouse and pointer, or by touch such as on a mobile device or tablet, for example. In the alternative, the representation 500 of the bed board may include (a) buttons 540 with which to reserve the associated by represented by bed number 530, (b) buttons 550 to indicate that the associated bed is now occupied, and buttons 560 to indicate that the bed is now available again.

When a registered users clicks on the representation 520 of the light button, a command to change the color of the light button is sent from the remote computing device to the server 410, and from the server to the particular bed board 100. Upon receipt, the particular light button 120 changes color to indicate the change in status, as defined by the remote user. In this manner, remote users may change the color of the light button or otherwise control the bed board in the same manner as a user actually touching the bed board. Since the commands and color changes are implemented in real-time, remote users are empowered with the same up-to-date information as a person physically standing next to the bed board. As stated above, the changes in availability status may be transmitted to and mirrored by light fixtures with green/yellow/red LED lights mounted at the hospital rooms or at the individual patient beds.

A redacted version of the interface may be used by doctors or other practitioners to reserve beds only. This interface would include "reserve" buttons 540, for example, but not the "occupied" buttons 550 or "clear" buttons 560. If a doctor desires to refer a client to a drug treatment center, for example, the doctor can check the digital version of the bed board to determine whether a bed is available in a particular drug treatment center and then reserve that bed online. The doctor need only download and log into a webpage configured to show the status of the beds of a given treatment center and then request a bed, if one is available. The webpage interface enables the doctor to see the number of available beds with a green light button. To reserve the bed, the doctor presses the "reserve" button on the webpage interface. A reservation request is then transmitted to designated facility personnel for approval by the appropriate facility authority(ies). When granted, the authority issues an authorization message to the server, which then confirms the reservation of the bed on behalf of the client of the doctor. The color of the light button associated with the reserved bed is changed to yellow in real-time, thus preventing hospital staff from assigning the bed to another person.

By way of another example, a police officer may take custody of person in need of non-emergency medical care. Using the present invention, the police officer may log into the server, download the webpage 500 corresponding to a particular hospital, and check the availability of one or more beds at that facility. When a bed is located, the officer may reserve the bed on behalf of the person in custody, and secure that bed (or room) when the approval is granted. If no bed is available at the first hospital, the police officer may search the system for one or more other hospitals in the vicinity until a bed is secured. The officer need only take the person to the facility for treatment at that point. This is a vast improvement over the prior art approach in which the police officer would often take the person to the hospital only to learn that no beds were available. At that point, the officer is confronted with the decision to drive to another hospital or wait for a bed to become available. Since the officer has the person in custody, the office must often remain with the person until a bed is available, which often represents a significant waste of time and resources for the officer.

Figure 6:
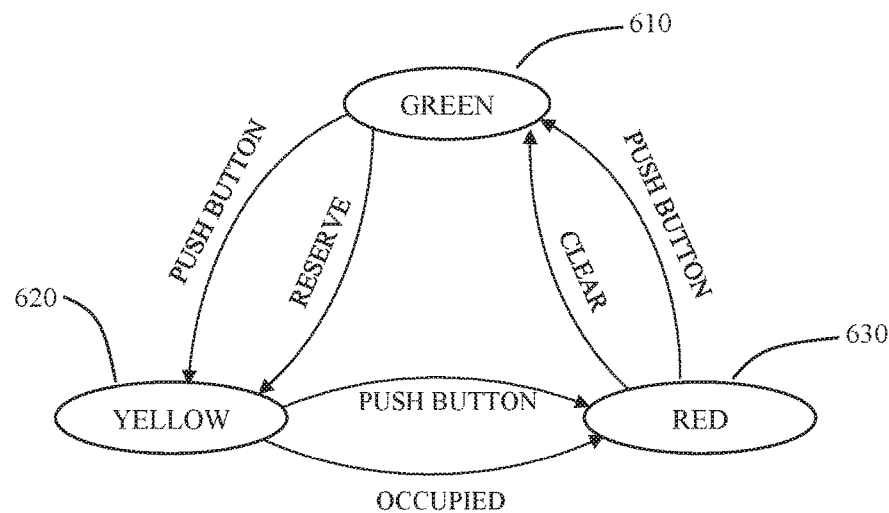
FIG. 6 is a state diagram illustrating the light modes for a light button, in accordance with one embodiment of the present invention.

Illustrated in FIG. 6 is a state diagram showing the transition of light modes for a light button, in accordance with one embodiment of the present invention. As explained above, the light may assume one of three different light colors, each representing a different state. The color of each light button is controlled by an individual state diagram, so different light buttons may be in different states at any given time.

The initial state is the green state 610 indicating that a bed is available. This green state is visible on the physical bed board displayed in the hospital facility as well as the virtual bed board displayed digitally via the web interface. The state of the light button may be changed to a yellow state 620 in response to either of two events: (a) the light button 120 is physically pushed or (b) the "reserve" button 540 or virtual light button 520 on the web interface is activated. Depending on configuration of the light button, the physical activation of the light button may automatically change the color, or may cause a change in color after the server generates a command to change the color.

If the virtual light button on the web interface is activated—and the reservation request approved—the server issues a command to change the color of light emitted by the physical light button on the bed board as well as the virtual light button on digital representation of the bed board seen by users on the web interface.

In some embodiments, the reservation of a bed must be approved by facility administration before the reservation is acted on or otherwise complete. Approval may be requested automatically by the server in the form of one or more emails, text messages, in-app notifications, and/or via system messages functions transmitted to the proper facility authority or authorities. All relevant patient and medical information may be transmitted to the proper facility authority(ies). The response from the authority(ies) may include a yes/no decision. If yes, the authority may assign a particular bed number, room number, house number, and/or facility number as part of the approval process. If and when approval is granted, the approval message is sent to the server. The server, in turn, issues a command to the bed board to cause the particular light button to emit yellow light. In addition, the proper authority may approve and/or forward to additional approval authority such as a medical director, who will also be notified via emails, text messages, in-app notifications, and/or via system messaging and asked for approval or rejection of the inbound patient. While this process is underway the corresponding light has turned yellow and the bed is no longer available in the system (meaning, a professional or public consumer can no longer find the bed in his or her search results).

Once set to the yellow state 620, the light button continues to emit yellow light to signify that the bed is reserved for an individual person. The state of the light button may be changed to a red state 630 in response to either of two events: (a) the light button 120 is physically pushed when the patient occupies the bed, or (b) the "occupied" button 550 or virtual light button 520 on the web interface is activated when the patient physically occupies the bed. If the virtual light button on the web interface is activated and the reservation request approved, the server issues a command to change the color of light emitted by the physical light button on the bed as well as the virtual light button on the web interface.

Once set to the red state 630, the light button continues to emit red light to signal that the bed is occupied by an individual person. The state of the light button may be changed to a green state 610 in response to either of two events: (a) the light button 120 is physically pushed when the patient no longer physically occupies the bed, or (b) the "clear" button 560 or virtual light button 520 on the web interface is activated when the patient no longer physically occupies the bed. If the virtual light button on the web interface is activated and the reservation request approved, the server issues a command to change the color of light emitted by the physical light button on the bed as well as the virtual light button on the web interface.

Figure 7:
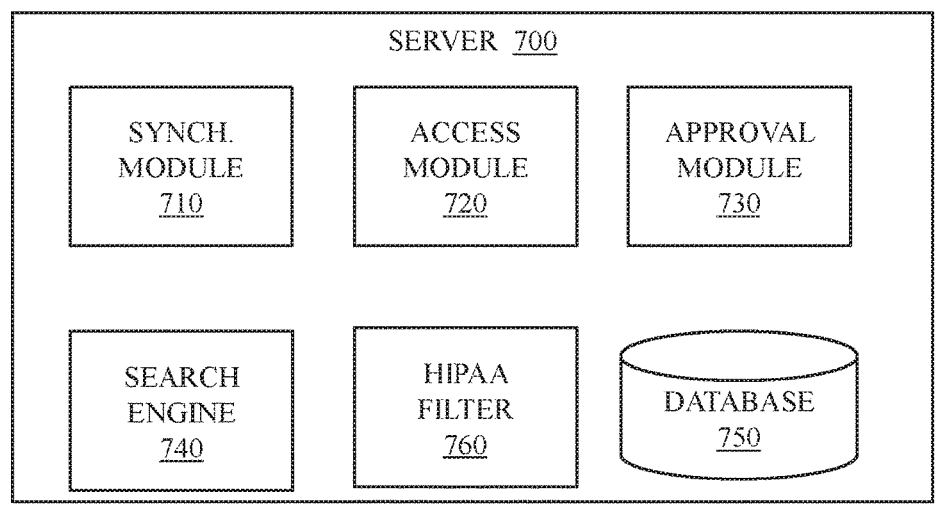
FIG. 7 is functional block diagram of a server for administering a light board in a communications network, in accordance with one embodiment of the present invention.

Illustrated in FIG. 7 is functional block diagram of a server for administering a light board in a communications network. The server, referred to herein as a state synchronization control (SSC) server 700, is configured to control and change the states of the light buttons of at least one bed board based on interaction with the bed board or any of a number of remote computing devices. In the preferred embodiment, the SSC server 700 comprises a synchronization module 710, an access module 720, an approval module 730 with approval criteria, a search engine 740, and a database 750 with patient data as well as a record of hospital resources and services, and a HIPAA display filter 760.

The synchronization module 710 is configured to monitor for messages from each of the associated light buttons, physical or virtual, indicating a change in status, and mirror that status to the other representations of the bed board (and to associated light fixtures adjacent to patent rooms or beds, if applicable). Similarly, the synchronization module monitors for messages from remote devices indicating that a person has pushed a virtual light button to change the color status. The synchronization module also determines whether any conditions, if applicable, have been met before changing the status. In the preferred embodiment, the synchronization module can change a light button status from green to yellow, from yellow to red, and from red to green. In the preferred embodiment, the synchronization module includes an approval module 730 with approval criteria. The approval criteria may identify one or more individuals in hospital administration that must approve a bed request and the contact information for those administrators. If the chief of nursing must approve a bed request, the approval module generates an email, text message, in-app notification, and/or system message to that person's contact address to obtain such approval. If and when the approval is granted via a dedicated message or text message, for example, the approval is transmitted to the SSC server and the color status changed from green to yellow. A complete list of criteria for approval, and relevant contact information, may be stored at the SSC server.

The access module 720 in the preferred embodiment is configured to regulate the access to the virtual representation 500 of the bed boards 100, what such people can see if they have access, and what such people can change if they have access. In general, access to the virtual representation is limited to licensed medical professionals that have registered with the SSC server 700. Medical professionals generally have the right to view available beds in one or more medical facilities and to request to reserve a bed in those facilities. They generally do not have, however, privileges to change the status associated with a bed to red or to green. Hospital staff generally have the right to view the status of all beds in those medical facilities in which they work or manage. Hospital staff may also have the privilege of changing the status of any bed from available to reserved, and occupied to available. Hospital administration generally have the highest access rights, which give them the privilege of viewing all beds and changing the status of any bed. This includes authorizing the reservation of a bed in response to a request by a medical professional, thus changing the status of a bed from green to red.

The approval module 730, together with the approval criteria, is configured to process reservation requests. This approval process begins with a request from a medical professional seeking to reserve a bed in a hospital, for example. Upon receipt, the approval module retrieves the contact information of one or more hospital administrators from which approval is required. The reservation request and relevant information is forwarded to those hospital administrators. The approval may include a bed assignment, for example. If and when approval is granted, the access module 730 communicates the approval to the synchronization module 710, which changes the status for the assigned bed from green to yellow. The status change is reflected in real-time at the associated bed board as well as the representations of the bed board being viewed via remote computing devices and mobile phones, for example. The approval module may be configured to send an approval communication to the medical professional requesting a bed.

In the preferred embodiment, the database 750 containing patient data including current medical information, past medical information from treatment at the present hospital, past medical treatment at other hospitals, and medical insurance coverage. Current medical information may include the patient name, admission date, age, gender, room assignment, primary therapist or doctor, estimated discharge date, contract/payment type, and date of next utilization review, for example. The database 750 of information enables hospital administrators to make informed decisions about the type of resources needed by the patient in order to best serve the patient.

In some embodiments, the SSC server 700 includes a search engine 740 for querying patient records as well as hospital resources and services. The search engine 740 may include a virtual digital interface that enables a medical professional to enter one or more hospital attributes which are then searched against the list of hospital resources and services to determine bed availability. The criteria that may be used to search for available hospital beds includes, but is not limited to, hospital name, address, approved insurance and funding type, price, facility size or number of beds, age range/age groups, and specific types of services available.

If a medical professional wants to locate a drug treatment center with a particular type of treatment option that also accepts a particular medical insurance plan, for example, the medical professional may use the search engine to locate medical facilities that meets all these criteria and have an available bed. The facilities that meet the criteria may be listed in a list of search results list and those results ranked based on their patient outcomes, the cost, the proximity of the facility, and the availability of a bed in that facility, for example. The list of search results are provided to the user based on the importance of the metrics or the relevance of the drug treatment center, for example. The search engine, therefore, enables professionals to easily and conveniently identify the best choice of hospital facility without any undue wait or a room to become available.

The SSC server may further include a HIPAA display filter 760 configured to limit the amount of personal information of a patient that is displayed in a public area, for example. Users must first login to the server system with their credentials and be authenticated before they can access any particular patient's medical data. The HIPAA filter is configured to limit user access to patient data unless that person is authorized to view that information as defined in applicable healthcare regulation. In some embodiments, bed boards are configured with LED displays that display a patient's name and other information alongside the light button next to the person's name. In this embodiment, the HIPAA filter is configured to redact the information displayed on the bed board in order to make the bed board display compliant with HIPAA regulations. For example, the HIPAA filter may be configured to display only a patient's first name and date of birth in order to prevent the public present in the hospital from seeing confidential personal and medical information of persons being treated in the hospital.

Figure 8:
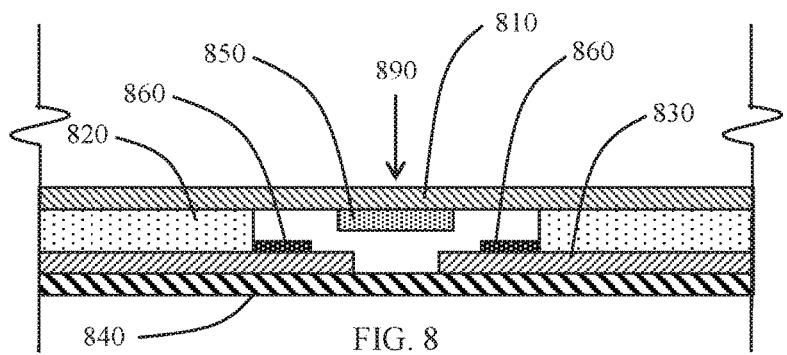
FIG. 8 is a cross section of a bed board with integrated light buttons, in accordance with a second embodiment of the present invention.

Illustrated in FIG. 8 is partial cross section of a bed board with integrated light buttons, in accordance with a second embodiment. The bed board includes a plurality of layers of elastomeric material that flex to form switches and circuits for light buttons. The plurality of layers preferably include a flexible writing surface 810, an non-conductive layer 820, a circuit layer 830, and a rigid backing 840. The flexible writing surface 810 is configured to be written on by dry-erase markers, for example, so hospital personnel may write patient data on the bed board. The flexible writing surface may also include one or more electrically conductive elements 850 coinciding with a button portion 890.

In this embodiment, the conductive element 850 is proximal to the circuit layer 830 but not in contact with the circuit layer. The conductive element 850 is held away from the circuit layer by the non-conductive layer 820, which is an electrical insulator. If and when the user depresses the writing surface with their finger at the button portion 890, for example, the conductive element 850 is forced toward the circuit layer 830 where it makes contact with two poles of an electrical switch. Contact between the conductive element 850 and the two poles completes a circuit configured to energize the LED lights 860 and change the color of the light emitted from those LEDs. In the preferred embodiment, the bed board may include a plurality of such light buttons for changing the color emitted by lights also integrated into or mounted on the bed board. Use of the integrated light buttons are particularly advantageous because they enable the same area on the bed board to be used as both a button and a writing surface.

In the preferred embodiment, the bed board and server are configured to track and display the availability of beds in medical treatment facilities. In other embodiments, the system is configured to track availability of beds, seats, chairs, space, and rooms in other facilities including treatment centers, boarding care facilities, homeless shelters, hotels, hostels, restaurants, prisons, retail facilities, commercial facilities, transportation systems including planes and trains, for example.

Portions of the system can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium comprise a semiconductor or solid-state memory, magnetic tape, a removable computer diskette, a random access memory (RAM), a read-only memory (ROM), a rigid magnetic disk and an optical disk. Current examples of optical disks comprise compact diskread only memory (CD-ROM), compact disk-read/write (CD-R/W) and DVD.

A data processing system suitable for storing and/or executing program code comprises at least one processor coupled directly or indirectly to memory elements through a system bus. The memory elements can include local memory employed during actual execution of the program code, bulk storage, and cache memories that provide temporary storage of at least some program code in order to reduce the number of times code is retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Described above, aspects of the present application are embodied in a World Wide Web ("WWW") or ("Web") site accessible via the Internet. As is well known to those skilled in the art, the term "Internet" refers to the collection of networks and routers that use the Transmission Control Protocol/Internet Protocol ("TCP/IP") to communicate with one another. The internet 20 can include a plurality of local area networks ("LANs") and a wide area network ("WAN") that are interconnected by routers. The routers are special purpose computers used to interface one LAN or WAN to another. Communication links within the LANs may be wireless, twisted wire pair, coaxial cable, or optical fiber, while communication links between networks may utilize 56 Kbps analog telephone lines, 1 Mbps digital T-1 lines, 45 Mbps T-3 lines or other communications links known to those skilled in the art.

Furthermore, computers and other related electronic devices can be remotely connected to either the LANs or the WAN via a digital communications device, modem and temporary telephone, or a wireless link. It will be appreciated that the internet comprises a vast number of such interconnected networks, computers, and routers.

The Internet has recently seen explosive growth by virtue of its ability to link computers located throughout the world. As the Internet has grown, so has the WWW. As is appreciated by those skilled in the art, the WWW is a vast collection of interconnected or "hypertext" documents written in HTML, or other markup languages, that are electronically stored at or dynamically generated by "WWW sites" or "Web sites" throughout the Internet. Additionally, client-side software programs that communicate over the Web using the TCP/IP protocol are part of the WWW, such as JAVA® applets, instant messaging, e-mail, browser plug-ins, Macromedia Flash, chat and others. Other interactive hypertext environments may include proprietary environments such as those provided by online service providers, as well as the "wireless Web" provided by various wireless networking providers, especially those in the cellular phone industry. It will be appreciated that the present application could apply in any such interactive communication environments; however, for purposes of discussion, the Web is used as an exemplary interactive hypertext environment with regard to the present application.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A resource tracking system comprising:
   a. a board comprising:
      i. a re-writable surface;
      ii. at least one fastener configured to affix the re-writable surface to a wall;
      iii. a plurality of buttons arrayed in one or more rows or columns, wherein the plurality of buttons are affixed to the re-writable surface;
      iv. a plurality of lights arrayed in one or more rows or columns, wherein each of the plurality of lights is affixed to the re-writable surface and is operably coupled to one of the plurality of buttons;
      v. wherein each of the plurality of lights is configured to emit light of at least three colors, each color indicating a different status of an associated resource; and
      vi. a first network interface operably coupled to the plurality of buttons and plurality of lights;
      wherein the re-writable surface is configured to allow a plurality of patient names to be written thereon, with each of the patient names being writeable adjacent to one of the plurality of buttons and adjacent to one of the plurality of lights, which are each arrayed in one or more rows or columns to indicate the associated resource comprising one or more of a room or bed as being assigned to the patient names written adjacent to the respective buttons and lights; and
   b. a state synchronization control server comprising a processor and a second network interface, wherein the processor is configured with machine readable instructions configured to:
      i. generate an interactive display depicting:
         1. a representation of each of the plurality of buttons arrayed in one or more rows or columns;
         2. a representation of each of the plurality of lights arrayed in one or more rows or columns;
      ii. receive a first user command from the board to change a color emitted by a first light of the plurality of lights;
      iii. transmit the first user command to a remote computing device to change the color of the representation of the first light;
      iv. receive a second user command from the remote computing device to change a color emitted a second light of the plurality of lights;
      v. transmit the second user command to the board to change a color of said second light on the board; and
      vi. synchronize a color of the plurality of lights on the board and representation of said plurality of lights are on the board.

2. The resource tracking system of claim 1, wherein the re-writable surface is a whiteboard.

3. The resource tracking system of claim 2, wherein the resource is a bed in a medical facility.

4. The resource tracking system of claim 3, wherein each of the plurality of lights is integrally connected to one of the plurality of buttons, and wherein each of the plurality of lights is configured to emit at least three colors comprising green, yellow, and red color.

5. The resource tracking system of claim 1, wherein the first network interface comprises a wireless router.

6. The resource tracking system of claim 5, wherein the wireless router is configured to operably link the plurality of buttons and plurality of lights to the server.

7. The resource tracking system of claim 6, wherein the server is configured to operably link the board to a plurality of computers including the remote computing device.

8. The resource tracking system of claim 7, wherein the server is further configured to operably link the board to a plurality of computers via a cellular data network.

9. The resource tracking system of claim 8, wherein the cellular data network comprises a mobile phone network and the plurality of computers comprises at least one mobile phone.

10. The resource tracking system of claim 9, wherein the server and at least one mobile phone are configured to exchange short message service (SMS) messages.

11. The resource tracking system of claim 1, wherein the resource is a patient resource and the server comprises a database of information about a plurality of resources associated with the plurality of lights.

12. The resource tracking system of claim 11, wherein the resources associated with the plurality of lights include a plurality of beds, the information about the plurality of beds comprises types of medical services available to patients.

13. The resource tracking system of claim 12, wherein the server comprises a search engine configured to search the information about the plurality of beds based on queries from the remote computing device.

14. The resource tracking system of claim 13, wherein the database further comprises patient information.

15. The resource tracking system of claim 14, wherein the search engine is configured to search the patient information based on queries from the remote computing device.

16. The resource tracking system of claim 14, wherein the board further includes a digital display configured to present a portion of the patient information.

17. The resource tracking system of claim 16, wherein the server comprises a HIPAA filter, wherein the HIPAA filter is configured to prevent display of a portion of the patient information.

18. A resource tracking system comprising:
    a. a board comprising:
       i. a digital display;
       ii. at least one fastener configured to affix the digital display to a wall;

iii. a plurality of light buttons arrayed in one or more rows or columns;
iv. wherein each of the plurality of light buttons is configured to emit light of at least three colors comprising green, yellow, and red; each color indicating a different status of an associated resource; and
v. a first network interface operably coupled to the plurality of light buttons and plurality of lights;
wherein the re-writable surface is configured to allow a plurality of patient names to be written thereon, with each of the patient names being writeable adjacent to one of the plurality of buttons and adjacent to one of the plurality of lights, which are each arrayed in one or more rows or columns to indicate the associated resource comprising one or more of a room or bed as being assigned to the patient names written adjacent to the respective buttons and lights; and b. a server comprising a processor and a second network interface, wherein the processor is configured with machine readable instructions configured to:
 i. generate an interactive display depicting a representation of each of the plurality of light buttons and the color of each light button;
 ii. receive a first user command from the board to change a color emitted by a first light button of the plurality of light buttons;
 iii. transmit the first user command to a remote computing device to change a color of the representation of the first light button;
 iv. receive a second user command from a remote computing device to change a color emitted a second light button of the plurality of light buttons;
 v. transmit a second use command to the board to change a color of said second light button on the board; and,
 vi. synchronize a color of the plurality of lights on the board and representation of said plurality of lights are on the board.

19. A resource tracking system comprising:
a. a re-writable surface;
b. at least one fastener configured to affix the re-writable surface to a wall;
c. a plurality of buttons arrayed in one or more rows or columns, wherein the plurality of buttons are affixed to the re-writable surface;
d. a plurality of lights arrayed in one or more rows or columns, wherein each of the plurality of lights is affixed to the re-writable surface and is operably coupled to one of the plurality of buttons;
e. wherein each of the plurality of lights is configured to emit light of at least three colors, each color indicating a different status of an associated resource; and
f. wherein the re-writable surface is configured to allow a plurality of patient names to be written thereon, with each of the patient names being writeable adjacent to one of the plurality of buttons and adjacent to one of the plurality of lights, which are each arrayed in one or more rows or columns to indicate the associated resource comprising one or more of a room or bed as being assigned to the patient names written adjacent to the respective buttons and lights.

20. The resource tracking system of claim 19, wherein each one of said plurality of lights is integrally connected to one of said plurality of buttons.

* * * * *